United States Patent [19]

Hijiya et al.

[11] Patent Number: 5,530,155

[45] Date of Patent: Jun. 25, 1996

[54] PROCESS FOR RECOVERING L-PHENYLALANINE

[75] Inventors: Toyoto Hijiya; Chiaki Mochizuki; Tadashi Takemoto, all of Kawasaki; Kazutaka Nagashima, Yokkaichi, all of Japan

[73] Assignee: Ajinomoto Co., Inc., Tokyo, Japan

[21] Appl. No.: 409,980

[22] Filed: Mar. 24, 1995

[30] Foreign Application Priority Data

Mar. 24, 1994 [JP] Japan .................................. 6-053742

[51] Int. Cl.⁶ .................................................. C07C 229/34
[52] U.S. Cl. .............................. 560/41; 562/443; 562/445
[58] Field of Search ............................... 560/41; 562/443, 562/445

[56] References Cited

U.S. PATENT DOCUMENTS

| | | | |
|---|---|---|---|
| 4,803,300 | 2/1989 | Hijiya et al. | 560/41 |
| 5,118,840 | 6/1992 | Kano et al. | 560/41 |
| 5,304,671 | 4/1994 | Abe et al. | 560/41 |

FOREIGN PATENT DOCUMENTS

| | | |
|---|---|---|
| 0055612 | 7/1982 | European Pat. Off. . |
| 0526854 | 2/1993 | European Pat. Off. . |
| 2040473 | 1/1971 | France . |

OTHER PUBLICATIONS

Chemical Abstracts, vol. 109, No. 23, p. 710, Dec. 5, 1988, AN 211485u, JP-A-63 159 355, R. Mita, et al., "Recovery of L-Phenylalanine and L-Aspartic Acid from a Process for Aspartame Manufacture".

*Primary Examiner*—José G. Dees
*Assistant Examiner*—Joseph M. Conrad, III
*Attorney, Agent, or Firm*—Oblon, Spivak, McClelland, Maier & Neustadt

[57] ABSTRACT

Addition of a reaction mixture obtained by the mineral acid hydrolysis of at least one side flow generated from the production of α-L-aspartyl-L-phenylalanine methyl ester to a crystallization slurry containing L-phenylalanine while maintaining the pH of the slurry at 3–8 by adding aqueous alkali affords crystallized L-phenylalanine having a low water content in a high yield.

12 Claims, No Drawings

PROCESS FOR RECOVERING L-PHENYLALANINE

BACKGROUND OF THE INVENTION

1. Field of the Invention

The present invention relates to a process for producing α-L-aspartyl-L-phenylalanine methyl ester (hereinafter abbreviated as α-APM), which is about 200 times sweeter than sucrose and is extensively required as a sweetener due to its good sweet taste and low calorie content. More particularly, the present invention relates to a process for recovering L-phenylalanine (hereinafter abbreviated as L-Phe) from an aqueous solution such as a side flow (effluent) generated from a process for producing α-APM.

2. Discussion of the Background

Various processes for producing α-APM are known including, for example, a process which involves the reaction between an N-protected L-aspartic anhydride and L-phenylalanine methyl ester (U.S. Pat. No. 3,786,039), a process which involves the reaction between an N-protected L-aspartic anhydride and L-Phe (U.S. Pat. No. 4,173,562), and a process which involves the enzymatic condensation of N-benzyloxycarbonyl-L-aspartic acid and L-phenylalanine methyl ester (Japanese Patent Application Laid-Open No. 92729/1978).

However, in order for such processes to be useful as low-cost industrial processes, it is required to recover and reuse the L-Phe and L-aspartic acid (hereinafter abbreviated as L-Asp) contained in side flows (effluents) obtained from the production of α-APM, for example, the mother liquor from the crystallization of α-APM or the mother liquor from the crystallization of α-APM HCl since these side flows contain a significant amount of L-phenylalanine derivatives, L-aspartic acid derivatives, β-L-aspartyl-L-phenylalanine methyl ester and α-APM. Particularly, it is very important to efficiently recover L-Phe, which is an expensive amino acid.

A process for recovering L-Phe from the side flow generated from a process for the production of α-APM is disclosed in Japanese Patent Application Laid-Open No. 7812/1973. This process involves hydrolyzing a solution containing β-L-aspartyl-L-phenylalanine methyl ester in the presence of a mineral acid, adjusting the pH to about the isoelectric point of L-Phe, i.e., about 6, by adding aqueous alkali to the reaction solution to crystallize and separate L-Phe. To improve the yield of L-Phe during this crystallization step, it is required to increase the concentration of L-Phe in the hydrolyzate. However, in the neutralization process, L-Asp is also precipitated during the step of increasing the pH by adding aqueous alkali. Particularly, at a pH of about 1, L-Asp begins to crystallize, and the ability to stir the crystallization slurry becomes extremely difficult.

Increased concentration of L-Phe results in an increased concentration of L-Asp which exists in an almost equimolar amount to L-Phe. Accordingly, the solids content of the slurry becomes too high at the pH range around 1. In some cases, the entire or a portion of the crystallization slurry may become solidified and cannot be stirred. Accordingly, to improve the recovery of L-Phe, it is required to improve the ability to stir the slurry during the pH adjustment.

Moreover, in the conventional neutralization method, the deterioration of the ability to stir the slurry results in smaller L-Phe crystals. Further, the L-Phe crystals obtained after separation have a high water content. Using L-Phe with a high water content as a raw material for production of α-APM disadvantageously requires an extremely high load for drying when the L-Phe is recycled in the process described in U.S. Pat. No. 4,173,562. In addition, when L-phenylalanine is converted into its methyl ester for recycling, for example, as in the processes disclosed in U.S. Pat. No. 3,786,039 and Japanese Patent Application Laid-Open No. 92729/1978, the yield of ester may be lowered, because esterification is in equilibrium with hydrolysis.

Thus, there remains a need for an industrial process to recover L-Phe with a low water content in high yield when L-Phe is crystallized and recovered by neutralization from a mineral acid-hydrolyzed reaction solution of a side flow, generated from α-APM.

SUMMARY OF THE INVENTION

Accordingly, it is one object of the present invention to provide a method for recovering L-Phe.

It is another object of the present invention to provide a method for recovering L-Phe from a hydrolyzed reaction solution of a side flow from the production of α-APM.

It is another object of the present invention to provide a method for recovering L-Phe which results in L-Phe having a low water content.

It is another object of the present invention to provide a method for recovering L-Phe which exhibits a reduced tendency to experience stirring difficulties.

It is another object of the present invention to provide a method for recovering L-Phe which affords L-Phe in high yields.

These and other objects, which will become apparent during the following detailed description, have been achieved by the inventors' discovery that a process, in which a hydrolyzate and aqueous alkali are simultaneously added to an L-Phe slurry while maintaining the pH of the slurry at 5–6, provides a slurry with remarkably improved fluidity compared with that obtained by the conventional process in which the pH is adjusted by adding aqueous alkali to a solution, obtained by hydrolysis of a side flow of α-APM with a mineral acid, in the presence of a mineral acid. The present inventors have also found that when a hydrolyzate and aqueous alkali are simultaneously added to an L-Phe slurry while maintaining the pH of the slurry at about 3–8, L-Phe crystals with a reduced water content can be recovered in high yields.

That is, according to the present process, a hydrolyzate of strong acidity is rapidly brought to a pH of 3 to 8, at which the ability to stir is improved, without experiencing a pH of about 1, at which the ability to stir the crystallization slurry becomes difficult. By such a process, good slurry stirring is maintained even when using a hydrolyzate with such a high L-Phe concentration that the fluidity of the slurry would become extremely difficult and the slurry solidified when neutralized by the conventional method. Moreover, the crystallization yield of L-Phe from the resulting crystallization slurry is improved. In addition, the L-Phe crystals obtained by the present method have a remarkably reduced water content compared with those obtained by the conventional method.

Accordingly, the present invention provides a method for crystallizing L-Phe from an aqueous mixture comprising L-Phe and L-Asp and having a pH value lower than 0.1 by adding said aqueous mixture to a crystallization slurry comprising L-Phe while maintaining the pH of the crystallization slurry at a value of 3 to 8 by adding alkali to said slurry.

DETAILED DESCRIPTION OF THE PREFERRED EMBODIMENTS

Typical examples of the side flow obtained from the process for production of α-APM, which may be used to prepare the aqueous mixture comprising L-Phe and L-Asp and having a pH less than 0.1, include, for example, (i) a mother liquor obtained by crystallizing and separating α-APM from water, in which the α-APM was obtained by condensing N-benzyloxycarbonyl-L-aspartic anhydride and L-phenylalanine methyl ester, followed by deprotection by reduction (see U.S. Pat. No. 3,786,039);

(ii) a mother liquor obtained by crystallizing and separating α-APM. HCl precipitated upon treatment of a condensation product of N-formyl-L-aspartic anhydride and L-phenylalanine methyl ester at a high concentration with methanol and hydrochloric acid (see U.S. Pat. No. 4,684,745); and (iii) a mother liquor obtained by crystallizing and separating α-APM. HCl obtained by esterification of α-L-aspartyl-L-phenylalanine with water, methanol and hydrochloric acid (see U.S. Pat. No. 4,173,562).

These side flows may be hydrolyzed to form the aqueous mixture comprising L-Phe and L-Asp and having a pH less than 0.1. The mineral acids used to hydrolyze the contents of the side flow in the present invention include hydrochloric acid, sulfuric acid, phosphoric acid and the like. Considering the ease of removal of the salts generated by the adjustment of pH after hydrolysis, hydrochloric acid is preferred. During hydrolysis, the concentration of these acids is preferably 1–12N, particularly 2–6N. The amount used is desirably more than 1 mole, particularly 1.5 to 10 mole based on 1 mole of amino acid and amino acid residue contained in said side flow.

The concentration of L-Phe in the hydrolyzate is not particularly limited so long as said hydrolysate is obtained by hydrolysis at the above acid concentration. The present invention is particularly effective for a hydrolyzate having a L-Phe concentration above 8 g/dl, because at such concentrations, the reaction solution is readily solidified according to the conventional neutralization processes. Such hydrolyzates will typically contain L-Asp at a concentration above 7 g/dl. More preferably, the hydrolyzate contains L-Phe in a concentration greater than 10 g/dl and L-Asp in a concentration greater than 10 g/dl. The L-Phe and L-Asp concentrations are typically less than 20 g/dl.

The temperature for hydrolysis is 60°–120° C. Especially, 90°–110° C. is desirable. The reaction time may not be limited because it varies depending on various factors. However, too long a reaction time promotes racemization. Accordingly, a sufficient reaction time is typically within 20 hours. Typically, the hydrolyzate after the hydrolysis has a pH value not more than 2, more typically not more than 1.

The thus-obtained hydrolyzate is added to the crystallization slurry of L-Phe. When a hydrolyzate having a high L-Phe concentration is used, the hydrolyzate is desirably heated during addition to prevent crystallization.

During the addition of the hydrolyzate, the L-Phe slurry is maintained within the pH range of 3–8 by adding aqueous alkali. To improve the crystallization yield of L-Phe, it is desirable to adjust the pH of the obtained L-Phe slurry to a final value of 5–6 before solid-liquid separation, from the viewpoint of isoelectric point of L-Phe.

Suitable alkali used for the pH adjustment include sodium hydroxide, potassium hydroxide, sodium carbonate, ammonia and the like. Sodium hydroxide is most preferable from the viewpoint of cost. Solid alkali may be directly added. However, it is desirable to add the alkali in the form of an aqueous solution, because of the ease of pH adjustment.

The temperature of the crystallization slurry for pH adjustment is not particularly limited. The adjustment may be carried out at 0°–100° C., preferably at 0°–80° C. When it is carried out at a temperature above 10° C., it is desirable to cool the crystallization slurry to a final temperature below 10° C. after addition of hydrolyzate is complete, because the yield is improved by lowering the solubility of L-Phe.

The rate of addition of the hydrolyzate has no particular effect on the stirring ability of the slurry. However, in order to control the increase of temperature due to the heat generated upon neutralization of the strongly acidic hydrolyzate with the aqueous alkali, the whole of the hydrolyzate is desirably added over a period of one hour or more.

In the slurry containing L-Phe, to which the hydrolyzate and aqueous alkali are added, the concentration of L-Phe is not particularly limited. For example, water or an aqueous solution containing L-Phe may be used instead of an L-Phe slurry. In such cases, as the hydrolyzate and aqueous alkali are added, the concentration of L-Phe in the solution increases beyond its solubility, and L-Phe precipitates as crystals. Once some L-Phe has precipitated such addition is the same as addition to an L-Phe slurry.

Accordingly, the volume of L-Phe slurry to which the hydrolyzate is added is not particularly limited. On an industrial scale, any liquid volume may be employed, in which stirring using, for example, a stirring blade attached to an L-Phe slurry tank can be performed, and a pH meter functions effectively.

By means of the present process, L-Phenylalanine with less water content can be crystallized at a high yield by recovering L-phenylalanine by crystallization from a reaction mixture obtained by mineral acid hydrolysis of at least one side flow from the production of α-L-aspartyl-L-phenylalanine methyl ester, without any difficulty in the stirring of the crystallization slurry.

Other features of the invention will become apparent in the course of the following descriptions of exemplary embodiments which are given for illustration of the invention and are not intended to be limiting thereof.

EXAMPLES

Unless otherwise indicated, all % values given in the Examples are by weight based on the total weight of the solution, hydrolyzate, or slurry.

Example 1

A mother liquor from the crystallization of α-APM hydrochloride was heated at 105° C. for 7 hours to obtain a hydrolyzate solution. According to the analysis using an amino acid analyzer, the concentrations of L-Phe and L-Asp were 16.41 g/dl and 14.91 g/dl, respectively. The HCl concentration was 3.5N. 15 ml of this hydrolyzate was adjusted to pH 5.6 with 48% NaOH to prepare L-Phe slurry. This L-Phe slurry was stirred at 40° C., to which was added the same hydrolyzate (685 ml) over 10 hours. During this step, the pH of the crystallization slurry was maintained between 5 and 7 by addition of 48% NaOH. The pH after completion of addition of the hydrolyzate was adjusted to 5.6. The stirring ability during crystallization was not accompanied with any particular problems, providing a good slurry. During this step, the temperature was maintained at 38°–45° C. Then, the obtained L-Phe slurry was stirred at 6° C. for 24 hours, then separated by suction filtration. The crystals were washed with water (90 ml).

According to the analysis using an amino acid analyzer, 138.7 g of the resulting wet crystals contained 109.0 g of L-Phe. Yield, 94.9%. This wet crystals were dried at 105° C. for 4 hours. Loss on drying was 20.5%.

Comparative Example 1

The hydrolyzate obtained in Example 1 (300 ml) was stirred and heated in a 500 ml flask at 70° C., to which was added 48% NaOH. Around pH 0.7, crystals started to separate, resulting in extremely bad stirring ability.

In addition, the peripheral portion of the slurry was solidified and could not be stirred. 48% NaOH was further added to bring pH to 5.6. The peripheral portions of the mixture remained solidified. The peripheral solid was broken using a spatula and heated to 90° C. to give a slurry. This slurry was cooled to 5° C., stirred overnight, separated by suction filtration, and the resulting crystals were washed with water (40 ml). The resulting wet crystals (75.6 g) contained 46.1 g of L-Phe. Yield, 93.6%. Loss on drying, 37.2%.

Comparative Example 2

In the same manner as Example 1, a hydrolyzate solution was obtained from a mother liquor of α-APM. HCl crystallization. According to the analysis using an amino acid analyzer, the concentration of L-Phe is 17.0 g/dl. This hydrolyzate solution was diluted by addition of water to prepare 150 ml hydrolyzate solutions with L-Phe concentrations of 6, 8, 10, 13 and 15 g/dl, respectively. Each solution was charged in a 300 ml flask and stirred at 40° C. 48% NaOH was added to the solution and stirring ability of the slurry was examined until pH reaches to 5.6. A good slurry state was maintained only when hydrolyzate having an L-Phe concentration of 6 g/dl was used. When a hydrolyzate having an L-Phe concentration above 8 g/dl was used, the peripheral portion of the slurry was solidified around pH 1.

Example 2

35% HCl (140 g) was added to a mother liquor of an α-APM crystallization (25 L) and concentrated to 0.8 L under reduced pressure. 35% HCl (HCl concentration, 3.5N) was added to this concentrate and heated at 105° C. for 7 hours to obtain a hydrolyzate. According to the analysis using an amino acid analyzer, the concentrations of L-Phe and L-Asp were 18.35 g/dl and 15.29 g/dl, respectively. The separated mother liquor obtained in Example 1 (20 ml, containing 0.1 g of L-Phe) was stirred at 70° C., to which was added the hydrolyzate (600 ml) over 3 hours. During this addition, the pH of the crystallization slurry was maintained at 5-7 by addition of 48% NaOH. After addition of the hydrolyzate was complete, the pH was adjusted to 5.6. The stirring during crystallization was accompanied with no particular problem, providing a good slurry. The temperature during this addition was maintained at 68°-73° C. Thereafter, the resulting L-Phe slurry was stirred at 6° C. for 24 hours, the crystals were separated by suction filtration, and the separated crystals were washed with water (90 ml).

The resulting wet crystals (128.5 g) contained 104.9 g of L-Phe. Yield, 95.3%. Loss on drying, 16.1%.

Comparative Example 3

The hydrolyzate obtained in Example 2 (250 ml) was charged in a 500 ml flask, heated and stirred at 70° C., and 48% NaOH was added. Around pH 0.4, crystals suddenly began to separate out, resulting in extremely bad stirring ability and a solidified peripheral portion. Hot water (150 ml) was added to the flask. After a while, the solid became a slurry and could be stirred. Then, 48% NaOH was added to adjust the pH to 5.6. Subsequently, the reaction was cooled to 5° C., maintained at that temperature for 3 hours, and then separated by suction filtration. The thus-obtained crystals were washed with water (45 ml).

The resulting wet crystals (65.1 g) contained 41.1 g of L-Phe. Yield, 89.7%. Loss on drying, 34.8%.

Example 3

In the same manner as in Example 1, a hydrolyzate was obtained from a mother liquor of an α-APM. HCl crystallization. According to the analysis using an amino acid analyzer, the concentrations of L-Phe and L-Asp were 14.61 g/dl and 12.20 g/dl, respectively. The concentration of HCl was 4.0N. 20 ml of the hydrolyzate was adjusted to pH 3.5 with 48% NaOH to prepare an L-Phe slurry. This slurry was stirred at 40° C., to which was added the same hydrolyzate (480 ml) over 3 hours. During this addition, the pH of the crystallization slurry was maintained within 3.4-4.0 by addition of 48% NaOH. After the addition of the hydrolyzate was complete, stirring was continued at pH 3.5 for an hour. Then, the pH was adjusted to 5.6 with 48% NaOH. The stirring during crystallization was accompanied with no particular problems, providing a good slurry. The temperature during this step was maintained at 38°-45° C. Thereafter, the resulting L-Phe slurry was stirred at 6° C. for 5 hours, the crystals were separated by suction filtration, and the separated crystals were washed with water (50 ml).

The resulting wet crystals (79.0 g) contained 68.1 g of L-Phe. Yield, 93.2%. Loss on drying, 13.2%.

Example 4

In the same manner as in Example 1, a hydrolyzate was obtained from a mother liquor of an α-APM. HCl crystallization. According to the analysis using an amino acid analyzer, the concentration of L-Phe was 16.5 g/dl. A 1 L cylindrical vessel having an overflow hole at the level corresponding to 400 ml was equipped with a stirring blade, a thermometer, a pH meter and a dropping funnel containing 48% aqueous NaOH for neutralization. The hydrolyzate was continuously added to the cylindrical vessel at a rate of 100 ml/hr. During this step, the temperature of the solution was maintained at 37°-43° C., and pH was controlled at 5.3-5.6 by addition of 48% NaOH. Immediately after neutralization, the hydrolyzate became a slurry. On 3¼ hours after the beginning of the addition, the slurry began to overflow from the overflow hole. This slurry was collected in another vessel. This operation was continued for 7 hours. The slurry in the cylindrical vessel was cooled in a refrigerator overnight, then separated by suction filtration. The loss on drying of the resulting L-Phe crystals was 11.6%.

Example 5

The procedure of Example 4 was continued for 6 hours, except that a hydrolyzate having an L-Phe concentration of 14.9 g/dl was used and the pH was controlled to 4.2-4.5. Further, the resulting slurry was adjusted to pH 5.6, then crystallized in a refrigerator overnight and separated by suction filtration. The loss on drying of the resulting L-Phe crystals was 12.3%.

Example 6

The procedure in Example 5 was continued for 6 hours, except that the hydrolyzate was added at a rate of 200 ml/hr and the pH was controlled to 3.3–3.5. Further, the resulting slurry was adjusted to pH 5.6, then crystallized in a refrigerator overnight and separated by suction filtration. The loss on drying of the resulting crystals was 18.7%.

This application is based on Japanese Patent Application No. 053742/1994, filed on Mar. 24, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A process for crystallizing L-phenylalanine, comprising:

adding a hydrolyzed reaction mixture to a crystallization slurry comprising L-phenylalanine while maintaining the pH of said slurry at 3 to 8 by adding alkali to said slurry, to obtain crystals of L-phenylalanine, wherein said reaction mixture is obtained by hydrolyzing a side flow obtained during production of α-L-aspartyl-L-phenylalanine methyl ester, in the presence of a mineral acid.

2. The process of claim 1, wherein said mineral acid is hydrochloric acid.

3. The process of claim 1, wherein said L-phenylalanine is present in said hydrolyzed reaction mixture in an amount not less than 8 g/dl.

4. The process of claim 1, wherein said side flow obtained during production of α-L-aspartyl-L-phenylalanine methyl ester is selected from the group consisting of:

(i) a mother liquor obtained by crystallizing and separating α-L-aspartyl-L-phenylalanine methyl ester, and (ii) a mother liquor obtained by crystallizing and separating α-L-aspartyl-L-phenylalanine methyl ester HCl.

5. A method for crystallizing L-phenylalanine from an aqueous mixture, comprising:

adding (a) an aqueous mixture comprising L-phenylalanine and L-aspartic acid and having a pH less than 0.1 to (b) a crystallization slurry comprising crystalline L-phenylalanine, while maintaining the pH of said crystallization slurry at 3 to 8, by adding alkali, to obtain L-phenylalanine crystals.

6. The method claim 5, wherein said L-phenylalanine is present in said aqueous mixture in a concentration 8 to 20 g/dl and said L-aspartic acid is present in said aqueous mixture in a concentration of 7 to 20 g/dl.

7. The method of claim 5, wherein said alkali is NaOH.

8. The method of claim 5, wherein said crystallization slurry is obtained by adding a portion of said aqueous mixture and said alkali to water.

9. The method of claim 5, wherein said crystallization slurry is obtained by adding said alkali to a portion of said aqueous mixture.

10. The method of claim 5, wherein said aqueous mixture is obtained by hydrolyzing an aqueous solution comprising α-L-aspartyl-L-phenylalanine methyl ester with a mineral acid.

11. The method of claim 10, wherein said mineral acid is hydrochloric acid.

12. The method of claim 10, wherein said aqueous solution is selected from the group consisting of:

(i) a mother liquor obtained by crystallizing and separating α-L-aspartyl-L-phenylalanine methyl ester, and (ii) a mother liquor obtained by crystallizing and separating α-L-aspartyl-L-phenylalanine methyl ester HCl.

* * * * *